United States Patent
Starkebaum et al.

(10) Patent No.: US 7,252,665 B2
(45) Date of Patent: Aug. 7, 2007

(54) ABLATION OF STOMACH LINING TO REDUCE STOMACH ACID SECRETION

(75) Inventors: Warren L. Starkebaum, Plymouth, MN (US); Thomas R. Prentice, Lake Elmo, MN (US)

(73) Assignee: Medtronic, Inc, Minneapolis, MN (US)

( * ) Notice: Subject to any disclaimer, the term of this patent is extended or adjusted under 35 U.S.C. 154(b) by 213 days.

(21) Appl. No.: 10/698,223

(22) Filed: Oct. 31, 2003

(65) Prior Publication Data

US 2005/0096713 A1    May 5, 2005

(51) Int. Cl.
    *A61B 18/14* (2006.01)
(52) U.S. Cl. ............... 606/41; 607/101; 607/133
(58) Field of Classification Search ............ 606/41, 606/48–50; 607/101–102, 133
    See application file for complete search history.

(56) References Cited

U.S. PATENT DOCUMENTS

| 4,279,906 A | 7/1981 | Frosch et al. | |
| 4,869,902 A | 9/1989 | Buehler et al. | |
| 5,188,104 A | 2/1993 | Wernicke et al. | |
| 5,403,326 A | 4/1995 | Harrison et al. | |
| 5,423,872 A | 6/1995 | Cigaina | |
| 5,505,730 A | 4/1996 | Edwards | |
| 5,569,241 A | 10/1996 | Edwards | |
| 5,738,683 A * | 4/1998 | Osypka ................ | 606/47 |
| 5,782,798 A | 7/1998 | Rise | |
| 5,827,273 A | 10/1998 | Edwards | |
| 6,006,755 A * | 12/1999 | Edwards ............... | 128/898 |
| 6,159,146 A | 12/2000 | El Gazayerli | |
| 6,183,776 B1 | 2/2001 | Depui et al. | |
| 6,254,598 B1 * | 7/2001 | Edwards et al. ........ | 606/41 |
| 6,258,087 B1 * | 7/2001 | Edwards et al. ........ | 606/41 |
| 6,405,732 B1 * | 6/2002 | Edwards et al. ........ | 128/898 |
| 6,425,887 B1 | 7/2002 | McGuckin et al. | |
| 6,427,082 B1 | 7/2002 | Nordstrom et al. | |
| 6,427,089 B1 | 7/2002 | Knowlton | |
| 6,535,764 B2 * | 3/2003 | Imran et al. ........... | 607/40 |
| 2002/0065512 A1 * | 5/2002 | Fjield et al. ........... | 606/27 |
| 2002/0103424 A1 * | 8/2002 | Swoyer et al. ......... | 600/350 |
| 2002/0128636 A1 * | 9/2002 | Chin et al. ............. | 606/16 |

(Continued)

FOREIGN PATENT DOCUMENTS

| WO | WO 00/69376 | 11/2000 |
| WO | WO 01/87335 | 11/2001 |

OTHER PUBLICATIONS

"Stomach 'Pacemaker' May Suppress Appetite," story.news.yahoo.com/news?tmpl=story&cid=541&e=6&u=/ap/tummy_pacemaker.

(Continued)

*Primary Examiner*—Michael Peffley
*Assistant Examiner*—Alex Toy
(74) *Attorney, Agent, or Firm*—Mary P. Bauman

(57) ABSTRACT

The invention provides methods and devices to reduce stomach acid secretion in a patient with a hyper acid condition. For example, the invention may involve ablation of the stomach lining to destroy acid-producing cells. Destroying acid-producing cells may reduce the amount of stomach acid produced and, therefore the amount of acid refluxed in the esophagus. The invention may further provide methods and devices to monitor the esophageal acid level before and after the ablation procedure.

26 Claims, 6 Drawing Sheets

U.S. PATENT DOCUMENTS

2002/0183768 A1    12/2002  Deem et al.
2003/0009095 A1*    1/2003  Skarda ...................... 600/374
2003/0040804 A1     2/2003  Stack et al.
2003/0153905 A1*    8/2003  Edwards et al. .............. 606/41
2004/0215180 A1*   10/2004  Starkebaum et al. .......... 606/32
2004/0236381 A1*   11/2004  Dinsmoor et al. ............ 607/40

OTHER PUBLICATIONS

Stedman's Medical Dictionary, 26th Edition, p. 280.

* cited by examiner

ABLATION OF STOMACH LINING TO REDUCE STOMACH ACID SECRETION

FIELD OF THE INVENTION

The invention relates generally to surgical techniques affecting the stomach, and, more particularly, to surgical techniques for reducing stomach acid secretion.

BACKGROUND

A variety of medical approaches have been devised for reduction of acid secretion and therefore, treatment of gastroesophageal reflux disease (GERD), including diet, medication and surgery. In general, surgery is reserved for patients in whom conservative measures, such as monitoring eating habits or controlling acid levels with acid suppressant medications, have failed. In addition, surgery is generally reserved for patients who have severe cases of GERD and/or suffer from Barrett's esophagus, a precancerous condition linked to GERD.

Acid is one of the key fluids secreted by the gastrointestinal tract for digestion of food. Stomach acid is produced by parietal cells in the mucosal lining of the stomach. Reflux of stomach acid into the lower portion of the esophagus results in well known symptoms of GERD. A common medical strategy for treating GERD is to administer drugs which suppress the production of acid with histamine receptor antagonists or proton pump inhibitors. U.S. Pat. No. 6,183,776 to Depui, et al., for example, describes an oral pharmaceutical dosage for the suppression of stomach acid that includes proton pump inhibitors (PPI's). In another example, U.S. Pat. No. 4,279,906 to Frosch, et al. describes a histamine receptor antagonist (H2 blocker) agent to treat gastric diseases. In many cases, one of these two classes is effective in relieving symptoms of GERD. Some patients, however, do not wish to be on these GERD drugs indefinitely due to uncertain long-term effects. Additionally there are some patients who do not respond to drug treatment.

Other treatments available for GERD involve surgical techniques that strengthen the lower esophageal sphincter (LES), which acts as a valve between the stomach and the esophagus. U.S. Pat. No. 5,403,326 to Harrison, et al. describes a method for inhibiting acid reflux into the esophagus by performing a gastric wrap or fundoplication surgery. Surgical interventions such as this are very invasive, and any form of surgery may involve complications. In addition, surgical procedures often require recovery time that prevents the patient from immediately returning to normal lifestyle. Another surgical technique is described in U.S. Pat. No. 6,405,732 to Edwards, et al. in which the LES is tightened to block acid reflux by ablating nerves in the stomach, causing the LES to contract.

Table 1 below lists documents that disclose techniques for reduction of stomach acid secretion and treatment of GERD.

TABLE 1

| Patent Number | Inventors | Title |
| --- | --- | --- |
| 5,403,326 | Harrison, et al. | Method for performing a gastric wrap of the esophagus for use in the treatment of esophageal reflux |
| 6,159,146 | El Gazayerli | Method and apparatus for minimally-invasive fundoplication |
| 4,279,906 | Frosch, et al. | Indomethacin-antihistamine combination for gastric ulceration control |

TABLE 1-continued

| Patent Number | Inventors | Title |
| --- | --- | --- |
| 6,183,776 | Depui, et al. | Oral pharmaceutical dosage forms comprising a proton pump inhibitor and an antacid agent or alginate |
| 4,869,902 | Buehler, et al. | Antacid composition |
| 6,405,732 | Edwards, et al. | Method to treat gastric reflux via the detection and ablation of gastro-esophageal nerves and receptors |

All documents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY

The present invention is directed to devices and methods for reducing stomach acid secretion. The invention has certain objects. That is, various embodiments of the present invention provide solutions to one or more problems existing in the prior art with respect to treatment of excess acid production and gastroesophageal reflux disease (GERD).

The problems include, for example, the limited efficacy and uncertain side effects of conventional stomach acid suppressant medications, and the need for potential repeated dosages of such medications by the patient. Additional problems relate to the general undesirability, invasiveness, infection risk, and recovery time associated with conventional surgical techniques for treatment of GERD, such as fundoplication, and other techniques for strengthening the valve between the stomach and the esophagus.

Various embodiments of the present invention have the object of solving at least one of the foregoing problems. For example, objects of the present invention provide methods and devices for reducing acid secretion and treating GERD that are less invasive and present shortened recovery times for patients. As a further object, the invention seeks to inhibit stomach acid production with increased efficacy over an extended period of time. As an example, an object of the invention includes the ability to reduce the amount of acid produced by destroying acid-producing cells within the stomach lining.

Various embodiments of the invention may possess one or more features capable of fulfilling the above objects. In general, the invention provides a method for reducing stomach acid secretion that involves ablating tissue from a mucosal lining within a stomach of a patient with an ablation probe sized for use with the stomach. The ablation of stomach tissue is carried out in order to destroy acid-producing cells. The esophageal acid levels are determined before and after ablation, and then compared to determine the success of the ablation procedure.

Devices for ablation of stomach tissue for reducing acid secretion may include a wide range of gastric ablation probes. The gastric ablation probe is inserted into a stomach of a patient via a catheter. In general, the gastric ablation probe is sized for use with the stomach to provide contact or non-contact ablation of selected regions of the mucosal stomach lining. The ablation probe may take the form of an electrode or array of electrodes for transmission of radio frequency electrical current, an optical waveguide for delivery of laser energy, a microwave antenna, a cryogenic probe, an internally heated probe, or the like. In addition, in some embodiments, the ablation probe may include a fluid delivery port for delivery of fluids to the ablation site for enhanced conductivity or cooling. The ablation probe may further include at least one vacuum port to immobilize a region of the stomach lining for ablation. The ablation level and depth can be controlled to selectively ablate different tissue regions of the stomach and thereby achieve desired effects in inhibiting acid production.

In addition, a pH monitor, such as a monitor deployed esophageally, determines the amount of acid refluxing into the esophagus and the need for reduced acid secretion. The pH monitor is inserted to the esophagus by a catheter to gather pH data before and after ablation. The data may be compared to verify the success of the ablation procedure.

In comparison to known implementations for treatment of excess acid and GERD, various embodiments of the present invention may provide one or more advantages. For example, the invention avoids the need for highly invasive, surgical alteration or reconstruction of the stomach, as presented by fundoplication, as well as associated patient recovery times. In addition, the invention does not require the administration of medication with uncertain side effects and prolonged dosage requirements. Rather, the invention provides an ablation treatment that reduces stomach secretion by destroying acid-producing cells within the mucosal lining of the stomach.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
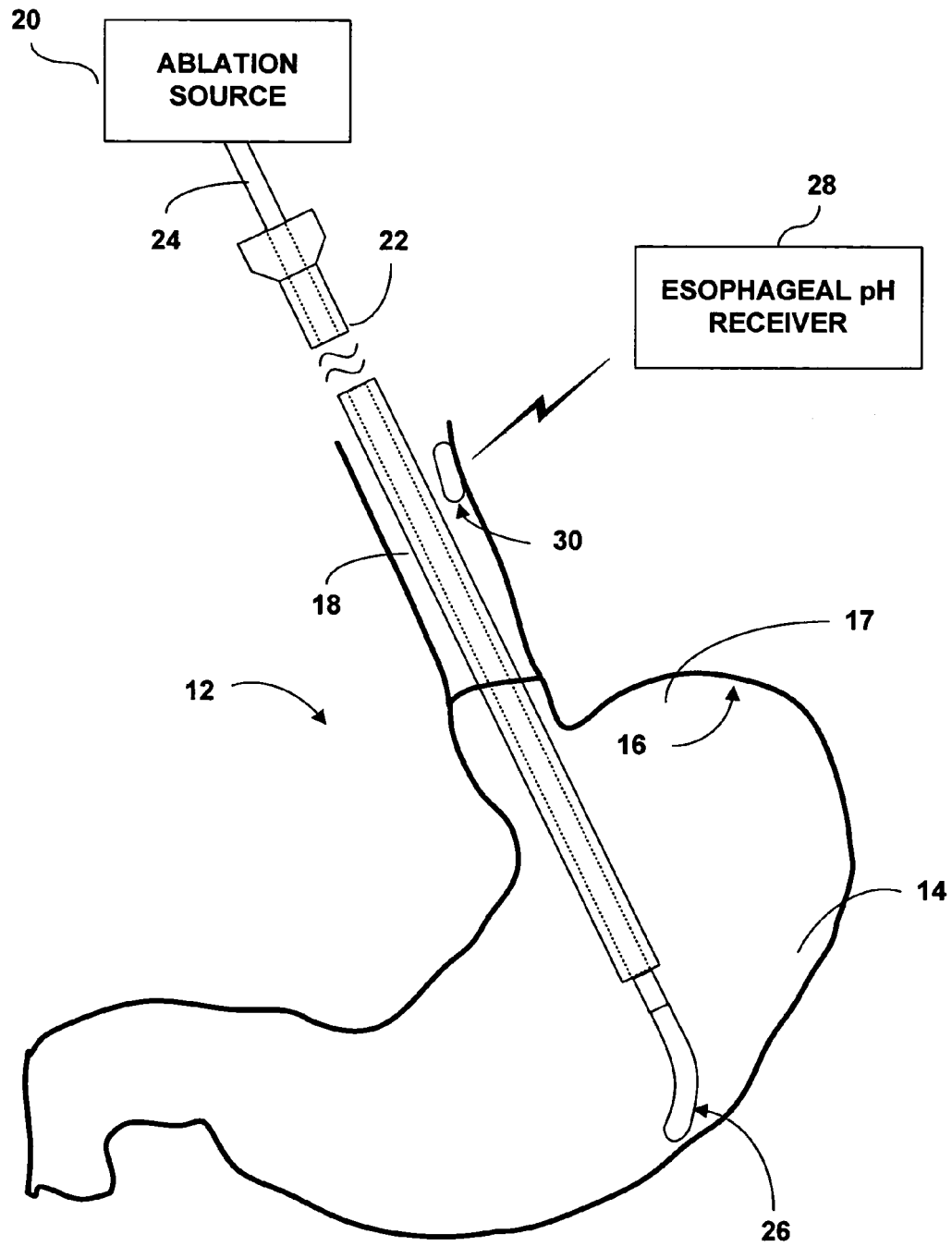
FIG. 1 is a schematic diagram illustrating a tissue ablation system for ablating a mucosal lining of a stomach to reduce stomach acid secretion.

FIG. 1 is a schematic diagram illustrating a tissue ablation system for ablating a mucosal lining 16 of a stomach 12 to reduce stomach acid secretion. There are multiple targets for ablation within stomach 12, which may be accomplished by appropriate positioning of an ablation probe 26, and by appropriate selection of ablation parameters. Ablating mucosal lining 16 within stomach 12 may inhibit the production of acid by the stomach tissue. Inhibiting acid production reduces the total amount of stomach acid available to reflux into esophagus 18. In this way, inhibiting acid production may reduce the occurrence and severity of the symptoms of gastroesophageal reflux disease (GERD).

As shown in FIG. 1, the ablation system includes a flexible, elongated catheter 22 sized for introduction into stomach 12 via an esophagus 18 of a patient. The ablation system also includes an ablation source 20 to power ablation probe 26 via a conductor 24. Ablation source 20 may comprise at least one of a radio frequency, laser, ultrasonic, microwave, thermal, chemical, mechanical, and cryogenic source for use with an appropriate ablation probe. Some embodiments of ablation source 20 include a reference electrode (not shown) placed on or within the patient, e.g., on the lower back or abdomen.

Ablation probe 26 and conductor 24 are inserted into stomach 12 through catheter 22. Ablation probe 26 is sized to fit stomach 12 of the patient, and accordingly catheter 22 is sized to fit ablation probe 26. Ablation probe 26 may be flexible or curved to further conform to a shape of the interior stomach wall at the target region. As shown in FIG. 1, for example, ablation probe 26 is sized to conform to the shape of the antrum 14.

As will be described, ablation probe 26 may comprise any of a variety of ablation probes that cooperate with ablation source 20, for example, an electrode for transmission of radio frequency electrical current, an optical waveguide for delivery of energy from a laser, a microwave antenna, a cryogenic probe, an internally heated probe, or the like. In addition, in some embodiments, ablation probe 26 may include a fluid delivery port for delivery of fluids to the ablation site for enhanced conductivity or cooling. In other embodiments, ablation probe 26 includes at least one vacuum port to immobilize a portion of mucosal lining 16 prior to ablation.

The ablation system further includes a pH monitor. An exemplary esophageal pH monitor, illustrated in FIG. 1, comprises a Bravo pH monitoring system commercially available from Medtronic, Inc., and includes an esophageal pH receiver 28 and an esophageal pH monitoring capsule 30 attached to esophagus 18. Monitoring capsule 30 is attached to the lining of esophagus 18 by a catheter, which is removed after placing monitoring capsule 30. Monitoring capsule 30 transmits pH data to receiver 28 carried by the patient. After a time, monitoring capsule 30 dislodges from the esophageal lining and passes in the patient's stool. The invention is not limited to the embodiment of esophageal pH monitor shown in FIG. 1. In another embodiment, a monitoring device is disposed on a tip of a nasal catheter, which is inserted to esophagus 18. A recorder is coupled to the monitoring device via the nasal catheter to store the pH data. In a further embodiment, the pH monitor is deployed at a site other than the esophagus, such as the interior of stomach 12.

Esophageal pH monitoring capsule 30 measures the reflux or regurgitation of acid from stomach 12 into esophagus 18 and transmits the measurements to esophageal pH receiver 28. Prior to ablating stomach 12, a first or baseline esophageal acid level is determined for the patient by monitoring the acid reflux with monitoring capsule 30. A period of time after the ablation, one week for example, a second or post-ablation esophageal acid level is recorded by again inserting a monitoring capsule 30. The period of time allows the gastro-intestinal (GI) tract to fully recover from the effects of any anesthetics used during the ablation procedure. The post-ablation esophageal acid level is compared to the baseline esophageal acid level to determine the success of the ablation procedure. Additional tissue may be ablated if the post-ablation esophageal acid level is not sufficiently lower than the baseline level. Use of the esophageal pH monitor before and after ablation provides a quantitative check of the effect of ablation on stomach acid secretion.

Ablating mucosal lining 16 within stomach 12 inhibits stomach acid production by destroying acid-producing parietal cells located within mucosal lining 16, and particularly in a fundus 17 of stomach 12. Destroying the acid-producing cells may reduce the symptoms associated with GERD. Reducing GERD symptoms may also reduce the possibility of developing Barrett's esophagus, which is a precancerous condition linked to prolonged acid reflux. The amount or area of tissue ablated in mucosal lining 16 of stomach 12 will determine the level of suppression of acid secretion and subsequent reduction of GERD symptoms. The energy level and depth of ablation may be selected and controlled by ablation source 20 to selectively ablate mucosal tissue 16, and thereby inhibit acid production. The effect of ablation of mucosal lining 16 may be measured by esophageal pH monitor 28, 30 that monitors and records the amount of acid refluxing into the esophagus of the patient.

FIGS. 2-9 are schematic diagrams illustrating exemplary ablation probes 26A-26H, respectively, for use with the tissue ablation system of FIG. 1. Catheter 22 and ablation probes 26A-26H may be positioned adjacent mucosal lining 16 of stomach 12 using endoscopic imaging techniques or external imaging techniques. For example, an endoscope may be integrated with catheter 22 to facilitate visualization of the area to be ablated, and aid in positioning of ablation probes 26A-26H relative to a target region within stomach 12. Catheter 22 and ablation probes 26A-26H are sized appropriately for use with stomach 12 and may be flexible or curved to further conform to the interior walls of stomach 12 or to reach a particular region of stomach 12 such as fundus 17.

Figure 2:
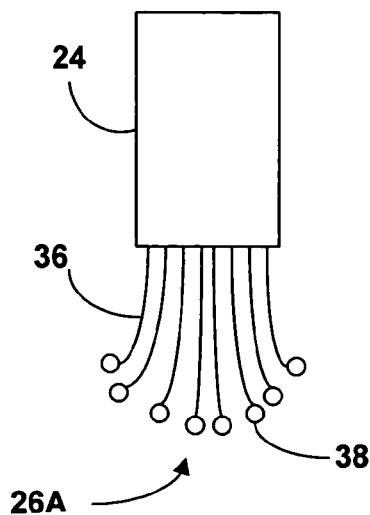
FIG. 2 illustrates an ablation probe comprising a plurality of flexible, electrically conductive filaments.

FIG. 2 illustrates an ablation probe 26A comprising a plurality of flexible, electrically conductive filaments 36. Each conductive filament 36 is coupled in common to conductor 24 to receive electrical current from ablation source 20, from FIG. 1. Conductive filaments 36 may carry spherical electrodes 38. In operation, when ablation probe 26A is placed in proximity to mucosal lining 16 of stomach 12, flexible filaments 36 extend outward and contact numerous points within a region of tissue to deliver electrical current and thereby ablate the tissue over a larger coverage area. The number of filaments 36 may vary. In addition, filaments may be arranged in a brush-like, two-dimensional array to cover a corresponding area of stomach tissue.

Figure 3:
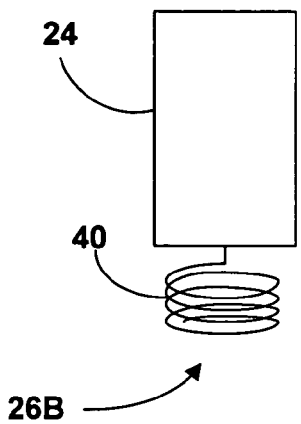
FIG. 3 illustrates an ablation probe comprising a flexible, helical or spiral wound conductive coil.

FIG. 3 illustrates an ablation probe 26B comprising a flexible, helical or spiral wound conductive coil 40 coupled to conductor 24. Upon contact with mucosal lining 16, coil 40 may compress and expand to more readily conform to a region of stomach 12. Coil 40 delivers electrical current from ablation source 20 to mucosal lining 16 and ablates the tissue in the target region. In other embodiments, coil 40 may have an expanded diameter at its base or its proximal end. In a further embodiment, coil 40 may be a closely wound, conductive coil with a very small diameter. One of the embodiments of coil 40 may be desired over the others to conform to a specific tissue region, or to create ablation sizes or shapes necessary to treat obesity.

Figure 4:
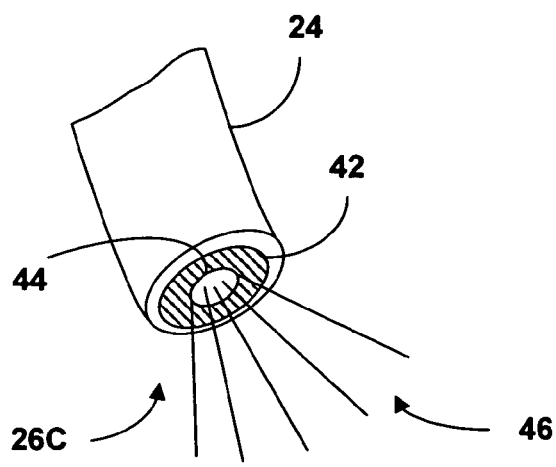
FIG. 4 illustrates an ablation probe comprising an electrode and a fluid delivery port.

FIG. 4 illustrates an ablation probe 26C comprising an electrode 42 and a fluid delivery port 44 coupled to conductor 24. Fluid delivery port 44 is coupled to a fluid source via a lumen within catheter 22, from FIG. 1, and delivers a stream of fluid 46. Electrode 42 delivers electrical current to mucosal tissue 16 via fluid 46. Fluid 46 may be electrically conductive to enhance the ablation result, and may be delivered at ordinary body temperatures or cooled temperatures. In this sense, ablation probe 26C may form a virtual electrode, e.g., as described in commonly assigned U.S. Pat. No. 6,537,272 to Christopherson et al., the entire content of which is incorporated herein by reference.

In some embodiments, ablation probe 26C includes a plurality of electrodes 42 and fluid delivery ports 44. The plurality of electrodes 42 and fluid ports 44 may be arranged in a pattern to enlarge the ablation area or to conform to one of the target regions within stomach 12.

Figure 5:
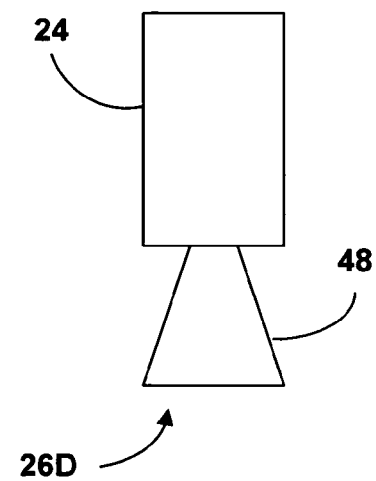
FIG. 5 illustrates an ablation probe comprising a waveguide.

FIG. 5 illustrates an ablation probe 26D comprising a waveguide 48 coupled to conductor 24. In that case ablation source 20 from FIG. 1 comprises a laser, and waveguide 48 further propagates the laser energy to mucosal lining 16 within stomach 12. The energy ablates the stomach tissue located within a proximate radius of waveguide 48. Waveguide 48 may comprise a variety of shapes and sizes to propagate specific wavelengths and modes of the laser energy.

Figure 6:
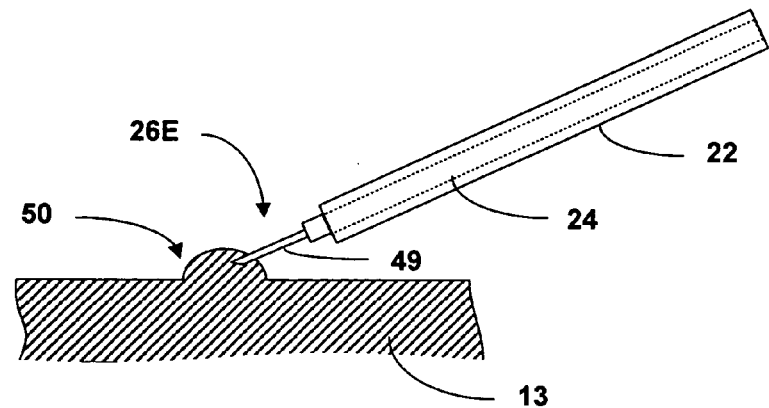
FIG. 6 is a diagram illustrating an ablation probe comprising a radio frequency ablation needle.

FIG. 6 is a diagram illustrating an ablation probe 26E comprising a radio frequency ablation needle 49 carried by conductor 24 via catheter 22. When ablation probe 26E reaches an ablation target within stomach 12 a surgeon inserts needle 49 into mucosal lining 16. In the example of FIG. 6, needle 49 is a hollow, conductive needle defining an inner lumen for delivery of fluid. In that embodiment, ablation probe 26E forms a virtual electrode within the tissue or manages cooling of surrounding tissue. In particular, electrical current may be accompanied by delivery of precise volumes of electrolytes to yield desired conduction characteristics.

The surgeon delivers the electrolyte fluid, such as saline, into mucosal tissue 16 via needle 49 to create a "blister" 50. The surgeon then activates ablation source 20, in this case an electrical current generator, to deliver electrical current to blister 50 via needle 49, and thereby ablate the tissue in the vicinity of the blister.

Figure 7:
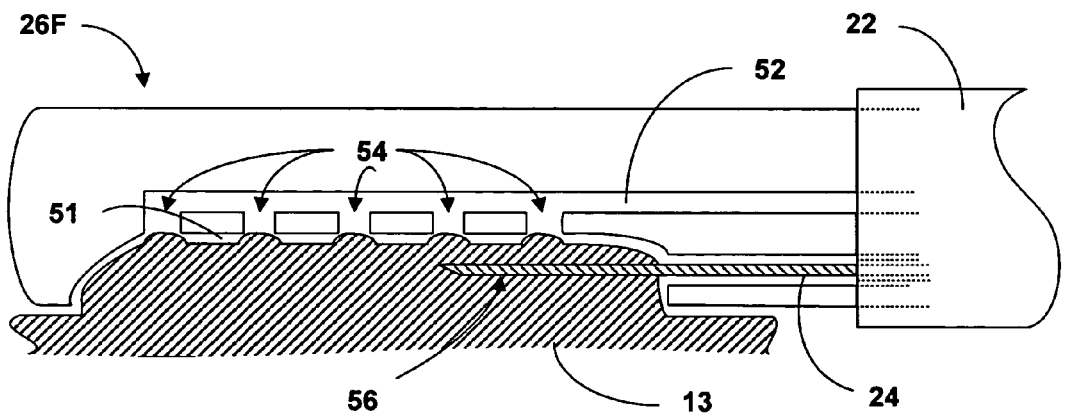
FIG. 7 is a side view illustrating an ablation probe comprising an array of vacuum ports to immobilize a portion of a mucosal lining of a stomach.

FIG. 7 is a side view illustrating an ablation probe 26F comprising an array of vacuum ports 54 to immobilize a portion of mucosal lining 16 of stomach 12. Ablation probe 26F includes a cavity 51, a vacuum line 52, vacuum ports 54, and a conductive needle 56. Conductive needle 56 couples to conductor 24 and may be a hollow needle defining an inner lumen for delivery of fluid, as described in reference to FIG. 6. Vacuum line 52 extends through catheter 22 and provides negative pressure from a vacuum source (not shown) to vacuum ports 54. When ablation probe 26F reaches an ablation target within stomach 12, the vacuum source activates to apply vacuum pressure to vacuum ports 54 to thereby draw the stomach tissue into cavity 51. The number and shape of vacuum ports 54, and the pressure applied by each vacuum port, may vary. While vacuum pressure is maintained, the surgeon extends conductive needle 56 into the captured stomach tissue.

In general, cavity 51 is sized and shaped to permit capture of a selected amount of stomach tissue by vacuum ports 54 for ablation. For example, cavity 51 may have different depths for selective ablation of the stomach tissue. In particular, ablation of mucosal lining 16 may require a relatively shallow cavity depth. In one embodiment, ablation probe 24F has a curved profile to better conform to a curvature of the interior wall of stomach 12.

In other embodiments the ablation energy may be laser, microwave, cryogenic, thermal, chemical, and the like to ablate cells within the captured tissue and the ablation probe may conform to the ablation energy source. In the embodiment shown in FIG. 7, the ablation energy is radio frequency electrical current applied to conductive needle 56. The electrical current may be selected to provide pulsed or sinusoidal waveforms, cutting waves, or blended waveforms. In addition, the electrical current may include ablation current followed by current sufficient to cauterize any blood vessels that may be compromised during the ablation process. Alternatively, in some embodiments, ablation probe 26F may take the form of a bipolar probe that carries two or more electrodes, in which case the current flows between the electrodes.

For ablation at various depths, the electrical current delivers power in the range of approximately 1 to 50 watts, and can be applied at a frequency of approximately 100 to 500 kHz, producing a temperature of approximately 50 to 100 degrees centigrade. To limit ablation of tissue to the target site, the ablation probe may include multiple temperature sensors for use in closed loop control of the ablation energy so that surrounding tissue can be maintained below 50 degrees centigrade. The size of and volume of the ablated tissue can be controlled by selection of an appropriate level of electrical current, and may be further controlled by delivery of fluids to form a virtual electrode that extends into interstitial areas and creates a greater overall electrode surface for conduction of ablation energy.

Figure 8:
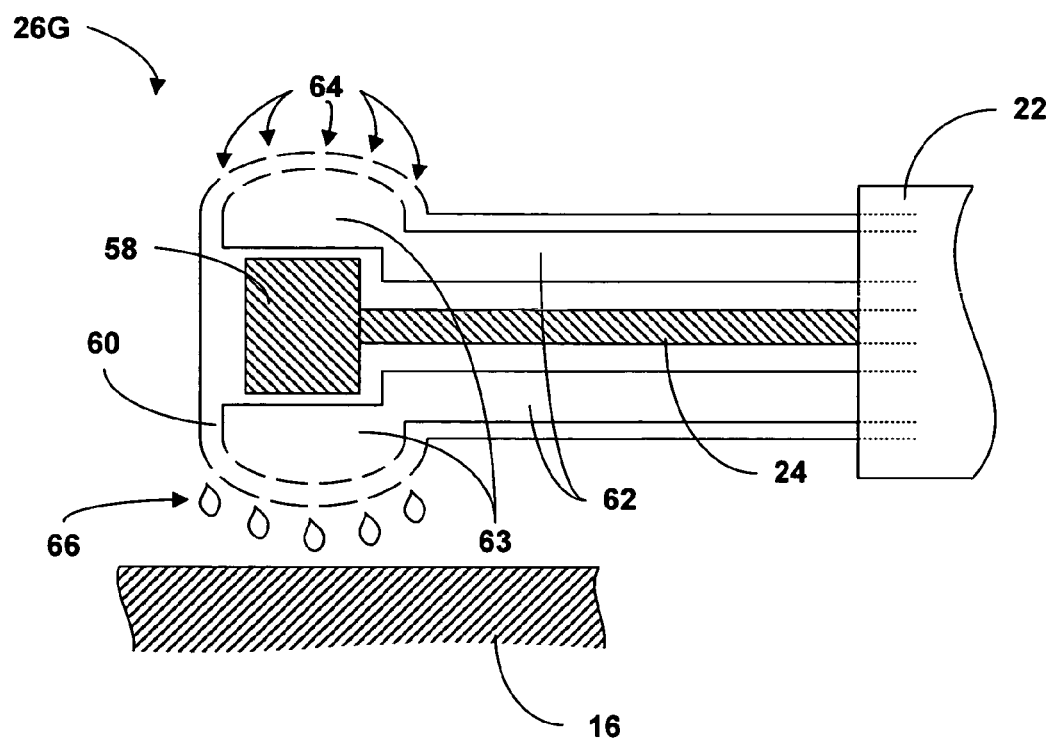
FIG. 8 is a side view illustrating an ablation probe comprising a porous balloon.

FIG. 8 is a side view illustrating an ablation probe 26G comprising a porous balloon 60. Ablation probe 26G includes an electrode 58, porous balloon 60, fluid channels 62, fluid chambers 63, and pores 64. Electrode 58 is coupled to ablation source 20, from FIG. 1, via electrical conductor 24. Porous balloon 60 is mounted about electrode 58. Balloon 60 defines pores 64 sized to permit a fluid 66 to leak at a relatively low flow rate from chambers 63. Fluid channels 62 deliver fluid to chambers 63 of balloon 60 to inflate the balloon. Balloon 60 may also have a temperature probe (not shown) located on an inside of the balloon so the fluid temperature can, if necessary, be precisely controlled.

Upon inflation of balloon 60, fluid 66 emits from pores 64, creating a collection of fluid 66 adjacent a tissue site of mucosal lining 16. In other words, balloon 60 is inflated with conductive fluid 66, which is allowed to weep out of pores 64, effectively increasing the surface area of electrode 58. Additionally, the fluid that weeps through balloon 60 serves to distribute heat generated by electrode 58 more evenly across the target tissue. Pores 64 are significantly enlarged in FIG. 8 for purposes of illustration.

In other embodiments, balloon 60 may be large enough to contact a circumferential area of stomach 12 when inflated. In that case, the surface area of electrode 58 may be further enlarged to ablate a substantial portion of mucosal lining 16 at one time.

Figure 9:
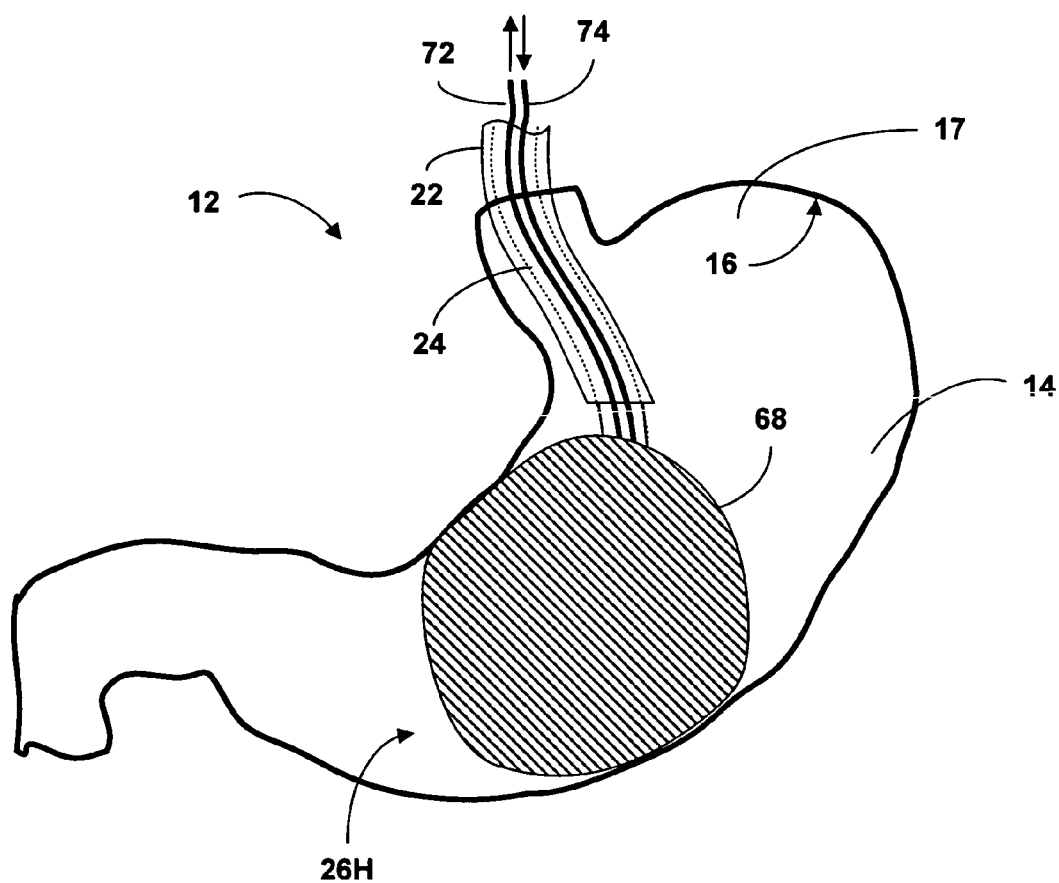
FIG. 9 is a diagram illustrating an ablation probe comprising a thermal balloon inflated to contact a circumferential surface of a mucosal lining of a stomach.

FIG. 9 is a diagram illustrating an ablation probe 26H comprising a thermal balloon 68 inflated to contact a circumferential surface of mucosal lining 16 of stomach 12. Ablation probe 26H includes thermal balloon 68, a fluid return 72, and a fluid supply 74. In the example shown in FIG. 9, conductor 24 conducts energy in the form of a thermal fluid received from ablation source 20, from FIG. 1. Fluid return and supply 72, 74 are coupled to ablation source 20. Thus, balloon 68 has an inlet and an outlet so fluid can be circulated from the external fluid source. The fluid source may provide either a hot fluid or a cryogenic fluid to ablation probe 26H. Conductor 24 may be thermally insulated to protect catheter 22 and prevent trauma to the throat and esophagus 18 of the patient.

When ablation probe 26H is placed proximate mucosal lining 16, fluid, such as water heated to approximately 50 to 60 degrees centigrade or liquid nitrogen, is then circulated within balloon 68 for a period of time. The time period ranges from approximately 10 seconds to 10 minutes, depending on the temperature of the fluid, and the depth of ablation desired. The flexible balloon 68 conforms to the shape of stomach 12 and thermal energy from the fluid is transmitted to mucosal lining 16 of stomach 12 through the wall of balloon 68 to ablate the stomach tissue in the contact regions.

In some embodiments, stomach 12 can be inflated through a port in catheter 22 so that balloon 68 intentionally does not make contact with the entire inner surface area of the stomach to avoid ablation of certain regions. In the embodiment shown in FIG. 9, balloon 68 is sized to contact a large proportion of mucosal lining 16. In this case, stomach 12 may be decompressed via a port in catheter 22 (not shown) so that a substantial portion of the inner surface of stomach 12 is in contact with balloon 68.

In other embodiments, balloon 68 may be placed in other regions of stomach 12 and inflated to contact the circumferential area of the regions. Further, balloon 68 may be shaped differently or smaller than shown in FIG. 9 so as to contact mucosal lining 16 on only one side, similar to balloon 60 from FIG. 8.

Figure 10:
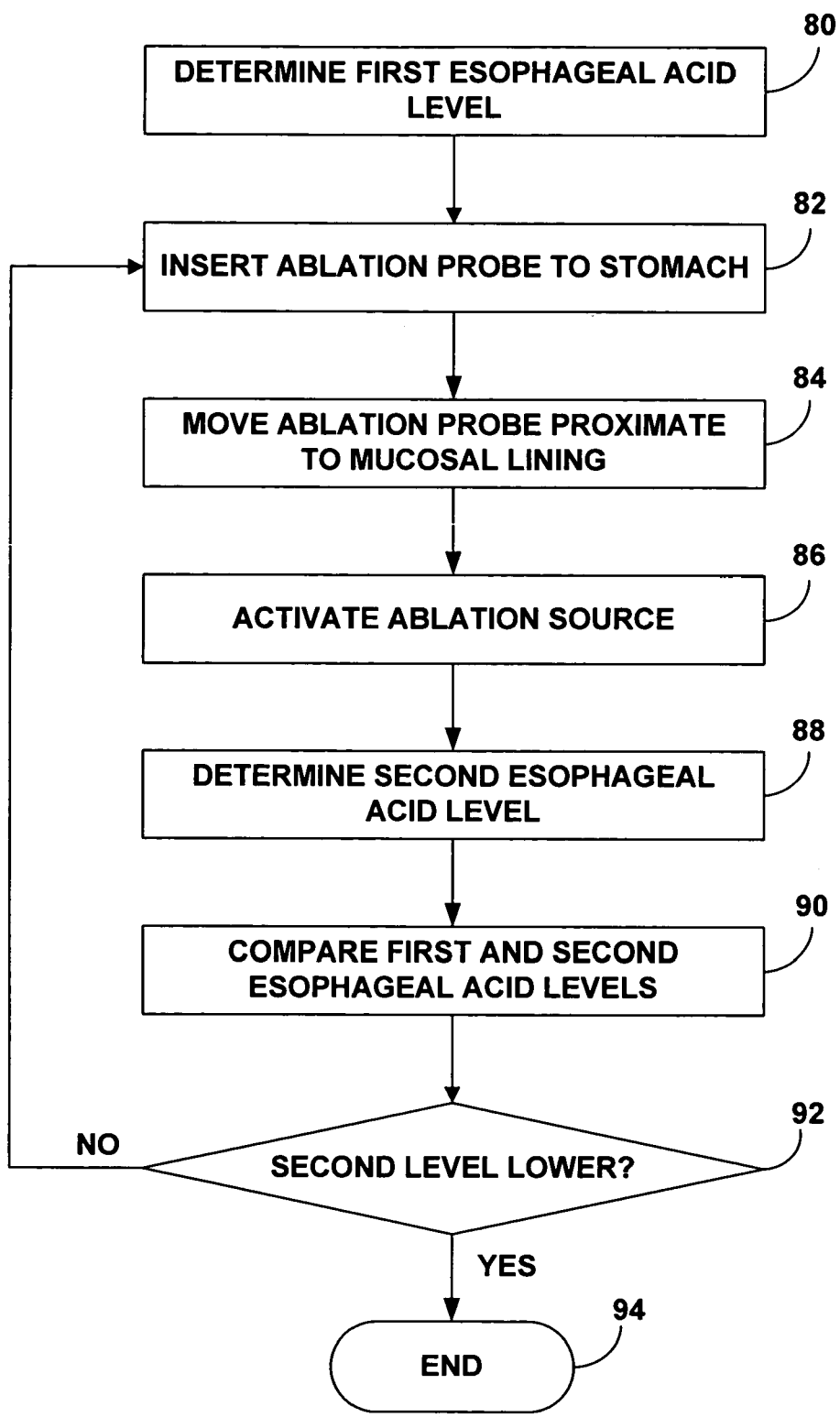
FIG. 10 is a flow diagram illustrating a method for ablation of a mucosal lining of a stomach to reduce stomach acid secretion.

FIG. 10 is a flow diagram illustrating a method for ablation of mucosal lining 16 of stomach 12 to reduce stomach acid secretion. The method of FIG. 10 may make use of any of the ablation probes 26A-26H described herein. A first or baseline esophageal acid level of the patient is determined (80) based on acid reflux levels in the esophagus monitored by esophageal pH monitoring capsule 30 and recorded by esophageal pH receiver 28. Ablation probe 26 is inserted into stomach 12 (82) of the patient through catheter 22, which may comprise an endoscope. The ablation probe 26 is moved proximate mucosal lining 16 of stomach 12 (84). Ablation source 20 is activated (86) to deliver ablation energy to ablation probe 26 and mucosal lining 16 to ablate stomach tissue and therefore, inhibit stomach acid production.

A period of time after the ablation procedure any sedative used during the ablation procedure will wear off and the GI tract of the patient will regain functionality. A second esophageal acid level may then be determined (88) by pH monitoring capsule 30 and pH receiver 28. The second esophageal acid level is compared to the first esophageal acid level (90). If the second esophageal acid level is lower than the first esophageal acid level (92), the ablation procedure was effective at reducing acid secretion and the ablation treatment may end (94). If the second esophageal acid level is not substantially slower than the first esophageal acid level, the ablation procedure was not effective and further stomach tissue may be ablated. In that case, a catheter 22 may again be inserted into stomach 12 (82) to begin another ablation treatment.

In other embodiments, steps may be added to the method shown in FIG. 10, including activating a vacuum source to immobilize a portion of mucosal lining 16 for ablation probe 26F. Additional examples include filling a balloon with fluid to either leak onto the stomach tissue prior to ablation as in ablation probe 26G, or to conduct thermal energy as in ablation probe 26H.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for ablation, as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method for reducing stomach acid secretion comprising:
   determining a first acid level of a patient with a hyperacid condition;
   temporarily impairing functionality of a gastro-intestinal tract of the patient;
   ablating tissue within a stomach with an ablation probe sized to fit the stomach to inhibit the production of acid by the tissue; and
   determining a second acid level of the patient following a period of time sufficient to allow the gastro-intestinal tract to regain functionality after ablation.

2. The method for reducing stomach acid secretion of claim 1, wherein determining the first acid level comprises monitoring acid reflux levels with an esophageal pH monitor.

3. The method for reducing stomach acid secretion of claim 1, wherein the first and second acid levels are first and second esophageal acid levels.

4. The method for reducing stomach acid secretion of claim 1, wherein inhibiting the production of stomach acid comprises reducing an amount of acid refluxed into an esophagus of the patient.

5. The method for reducing stomach acid secretion of claim 1, wherein the period of time after ablation comprises one week.

6. The method for reducing stomach acid secretion of claim 1, wherein ablating tissue comprises ablating at least a portion of a mucosal lining of the stomach.

7. The method for reducing stomach acid secretion of claim 1, wherein ablating tissue comprises ablating cells that produce stomach acid.

8. The method for reducing stomach acid secretion of claim 1, wherein ablating tissue comprises:
   inserting an ablation probe to the stomach via an esophagus of the patient;
   moving the ablation probe to a position proximate to a mucosal lining of the stomach; and
   activating the ablation probe to ablate at least a portion of the mucosal lining.

9. The method for reducing stomach acid secretion of claim 8, where the ablation probe comprises at least one of a radio frequency, laser, ultrasonic, microwave, thermal, chemical, mechanical, and cryogenic ablation probe.

10. The method for reducing stomach acid secretion of claim 8, wherein activating the ablation probe comprises delivering energy to the mucosal lining of the stomach via the ablation probe.

11. The method for reducing stomach acid secretion of claim 8, wherein the ablation probe comprises at least one electrode and wherein activating the ablation probe comprises delivering electrical current to the mucosal lining of the stomach via the electrode.

12. The method for reducing stomach acid secretion of claim 11, wherein the ablation probe comprises a conductive fluid delivery port adjacent the electrode, the method further comprises delivering the conductive fluid to the mucosal lining of the stomach prior to activating the ablation probe.

13. The method for reducing stomach acid secretion of claim 8, wherein the ablation probe includes an optical waveguide and wherein activating the ablation probe includes delivering energy from a laser to the mucosal lining via the optical waveguide.

14. The method for reducing stomach acid secretion of claim 8, wherein the ablation probe includes a cryogenic probe and wherein activating the ablation probe includes delivering cryogenic fluid to the mucosal lining via the cryogenic probe.

15. The method for reducing stomach acid secretion of claim 8, further comprising applying vacuum pressure to the mucosal lining to immobilize at least a portion of the mucosal lining.

16. The method for reducing stomach acid secretion of claim 8, wherein the catheter comprises an endoscope.

17. The method for reducing stomach acid secretion of claim 1, further comprising ablating additional stomach tissue based on a comparison of the second esophageal acid level to the first esophageal acid level.

18. The method for reducing stomach acid secretion according to claim 1, wherein temporarily impairing the functionality of the gastrointestinal tract comprises the administration of anesthetic to the gastro-intestinal tract.

19. The method for reducing stomach acid secretion according to claim 18, wherein the period of time is sufficient to allow the effects of the anesthetics to wear off.

20. The method for reducing stomach acid secretion according to claim 1, wherein the tissue within the stomach that is ablated is fundal tissue.

21. A method for reducing stomach acid secretion comprising:
   determining a first acid level of a patient with a hyperacid condition;
   ablating tissue within a stomach with an ablation probe sized to fit the stomach to inhibit the production of acid by the tissue;
   determining a second acid level of the patient one week after ablation; and
   comparing the second acid level with the first acid level to determine whether the second level is lower than the first acid level.

22. The method according to claim 21 further comprising ablating tissue within the stomach again if the second acid level is not sufficiently lower than the first acid level.

23. The method according to claim 21, wherein the first and second acid levels are first and second esophageal acid levels.

24. The method according to claim 21, wherein ablating tissue comprises ablating at least a portion of a mucosal lining of the stomach.

25. The method according to claim 21, wherein ablating tissue comprises ablating cells that produce stomach acid.

26. The method according to claim 21, where the ablation probe comprises at least one of a radio frequency, laser, ultrasonic, microwave, thermal, chemical, mechanical, and cryogenic ablation probe.

* * * * *